(12) United States Patent
Shokri et al.

(10) Patent No.: US 11,310,480 B2
(45) Date of Patent: Apr. 19, 2022

(54) SYSTEMS AND METHODS FOR DETERMINING THREE DIMENSIONAL MEASUREMENTS IN TELEMEDICINE APPLICATION

(71) Applicant: Proximie, Inc., Boston, MA (US)

(72) Inventors: Maryam Shokri, Winchester, MA (US); Talal Ali Ahmad, Bedford, MA (US)

(73) Assignee: PROXIMIE, INC., Boston, MA (US)

( * ) Notice: Subject to any disclaimer, the term of this patent is extended or adjusted under 35 U.S.C. 154(b) by 0 days.

(21) Appl. No.: 17/242,594

(22) Filed: Apr. 28, 2021

(65) Prior Publication Data

US 2021/0266518 A1 Aug. 26, 2021

Related U.S. Application Data (63) Continuation of application No. 16/541,799, filed on Aug. 15, 2019, now Pat. No. 11,025,889, which is a
(Continued)

(51) Int. Cl.
*H04N 13/271* (2018.01)
*G06T 7/60* (2017.01)
(Continued)

(52) U.S. Cl.
CPC ......... *H04N 13/271* (2018.05); *A61B 5/0013* (2013.01); *A61B 5/1072* (2013.01);
(Continued)

(58) Field of Classification Search
CPC ........ G16H 40/67; G16H 30/40; G16H 80/00; A61B 5/0013; A61B 5/1072;
(Continued)

(56) References Cited

U.S. PATENT DOCUMENTS 8,334,893 B2 12/2012 Hartman
2006/0262970 A1 11/2006 Boese et al.
(Continued)

OTHER PUBLICATIONS

International Search Report & Written Opinion in International Patent Application No. PCT/US17/35147, dated Jan. 11, 2018.
(Continued)

*Primary Examiner* — Neil R Mikeska
(74) *Attorney, Agent, or Firm* — Schmeiser, Olsen & Watts LLP; Timothy P. Collins (57) ABSTRACT

A system and method for measuring a depth or length of area of interest a telemedicine patient, comprising: a first image capturing device that captures a two-dimensional (2D) image or video of a region of interest of a patient; a second image capturing device that generates a three-dimensional (3D) point cloud of the region of interest of the patient; a rendering system that processes a unified view for both the first and second image capturing devices where the 2D image and 3D point cloud are generated and registered; and a remote measurement processing system that determines a depth or length between two points selected from the 2D image of the region of interest by identifying associated points in the 3D point cloud and performing a measurement using the identified associated points in the 3D point cloud.

17 Claims, 4 Drawing Sheets

Related U.S. Application Data continuation of application No. 15/609,538, filed on May 31, 2017, now Pat. No. 10,432,913.

(51) Int. Cl.
| | |
|---|---|
| *G06T 19/00* | (2011.01) |
| *G16H 40/67* | (2018.01) |
| *G16H 30/40* | (2018.01) |
| *A61B 5/00* | (2006.01) |
| *A61B 5/107* | (2006.01) |
| *H04N 13/246* | (2018.01) |
| *G16H 80/00* | (2018.01) |

(52) U.S. Cl.
CPC .............. *G06T 7/60* (2013.01); *G06T 19/006* (2013.01); *G16H 30/40* (2018.01); *G16H 40/67* (2018.01); *G06T 2207/10016* (2013.01); *G06T 2207/10028* (2013.01); *G06T 2207/30004* (2013.01); *G06T 2207/30196* (2013.01); *G16H 80/00* (2018.01); *H04N 13/246* (2018.05); *H04N 2213/003* (2013.01)

(58) Field of Classification Search
CPC ........... G06T 19/006; G06T 7/60; G06T 2207/10028; G06T 2207/30196; G06T 2207/10016; G06T 2207/30004; H04N 13/271; H04N 2213/003; H04N 13/246
See application file for complete search history.

(56) References Cited

U.S. PATENT DOCUMENTS

| | | |
|---|---|---|
| 2007/0247612 A1 | 10/2007 | Pack et al. |
| 2007/0297657 A1 | 12/2007 | Mattes et al. |
| 2010/0172567 A1 | 7/2010 | Prokoski |
| 2013/0223702 A1 | 8/2013 | Holsing et al. |
| 2013/0237811 A1 | 9/2013 | Mihailescu et al. |
| 2013/0249901 A1 | 9/2013 | Sweet et al. |
| 2015/0070470 A1 | 3/2015 | McMurrough |
| 2015/0287236 A1 | 10/2015 | Winne et al. |
| 2015/0341552 A1 | 11/2015 | Chen et al. |
| 2016/0037356 A1 | 2/2016 | Bathula et al. |
| 2016/0180743 A1 | 6/2016 | Ahmad |
| 2016/0187486 A1 | 6/2016 | Chen et al. |
| 2016/0307335 A1 | 10/2016 | Perry et al. |
| 2018/0096463 A1 | 4/2018 | Kim et al. |
| 2018/0131924 A1 | 5/2018 | Jung et al. |
| 2018/0225861 A1 | 8/2018 | Petkov et al. |
| 2018/0263707 A1 | 9/2018 | Sela et al. |
| 2018/0325601 A1 | 11/2018 | Mak et al. |
| 2018/0350073 A1 | 12/2018 | Shokri et al. |
| 2019/0236806 A1 | 8/2019 | Jiang et al. |

OTHER PUBLICATIONS

Non-Final Office Action in U.S. Appl. No. 15/609,538 dated Oct. 12, 2018.
Final Office Action in U.S. Appl. No. 15/609,538 dated Mar. 8, 2019.
Notice of Allowance in U.S. Appl. No. 16/541,799 dated Feb. 8, 2021.
Notice of Allowance in U.S. Appl. No. 15/609,538 dated Jun. 26, 2019.
International Preliminary Report on Patentability in PCT/US2017/035147, dated Dec. 12, 2019.
Non-Final Office Action in U.S. Appl. No. 16/541,799 dated Sep. 24, 2020.

SYSTEMS AND METHODS FOR DETERMINING THREE DIMENSIONAL MEASUREMENTS IN TELEMEDICINE APPLICATION

RELATED APPLICATIONS

This application is a continuation application of U.S. patent application Ser. No. 16/541,799 filed on Aug. 15, 2019, entitled "Systems and Methods for Determining Three Dimensional Measurements in Telemedicine Application," which is a continuation application of U.S. patent application Ser. No. 15/609,538 filed on May 31, 2017, now U.S. Pat. No. 10,432,913, entitled "Systems and Methods for Determining Three Dimensional Measurements in Telemedicine Application," the entirety of each of which is incorporated by reference herein.

FIELD

The present concepts relate generally to telemedicine, and more specifically, to a system and method for calculating a length, depth, or related measurement in a three dimensional point cloud generated in a telemedicine application.

BACKGROUND

Telemedicine refers to the practice of medicine at a distance where the patient and the medical professional are at different locations, and communicate via a computer network, or telecommunications system, which provides for the live exchange of information between the patient and medical professional locations. Applications may include tele-surgery, tele-mentoring, or related medical-related exchanges between users at different locations. A typical telemedicine environment includes a camera at a medical professional location that captures live or near real-time images of a patient, and transmits the images electronically to a computer at a remote location where a doctor or other medical professional may view the images on the computer's display screen, and provide medical services for the patient such as diagnosis, virtual assistance to a local surgeon, or even surgery, for example, with the assistance of robotic medical devices co-located with the patient and remotely controlled by the doctor.

Telemedicine operations such as diagnosis, surgery, teaching, and so on often present a challenge to the remote viewer of the displayed electronic images of the patient, in particular, with respect to determining from the images a length or depth of a wound, incision, skin lesion, or other region of interest to the remote medical professional viewing the images on the display screen.

BRIEF SUMMARY

In one aspect, a system for measuring a depth or length of a wound of a telemedicine patient, comprises a first image capturing device that captures a two-dimensional (2D) image of a region of interest of a patient; a second image capturing device that generates a three-dimensional (3D) point cloud of the region of interest of the patient; a rendering system that processes a unified view for both the first and second image capturing devices where the 2D image and 3D point cloud are generated and registered; and a remote measurement processing system that determines a depth or length between two points selected from the 2D image of the region of interest by identifying associated points in the 3D point cloud and performing a measurement using the identified associated points in the 3D point cloud.

In some embodiments, the system further comprises an overlay system that creates a render point map image computed using data from the first and second image capturing devices.

In some embodiments, the first and second image capturing devices are calibrated to produce intrinsic and extrinsic parameters, which in turn are used to create the render point map image.

In some embodiments, the system further comprises a database for storing the intrinsic and extrinsic parameters and calibration data, and other data.

In some embodiments, the system further comprises a set of fiducial markers used as reference points in the render point map image.

In some embodiments, the rendering system generates the render point map to map a 3D point cloud of a fiducial marker of the set of fiducial markers to a shared field of view (FOV) of the first and second image capturing devices to register 2D video of the markers with the image of the render point map and determine the set of 2D to 2D transformation parameters.

In some embodiments, the 2D video of the markers is used by the rendering system for executing a registration process, including a registration to create transformation parameters to transform point coordinates selected from the video to render point map image and find them in 3D point cloud by executing a search algorithm.

In some embodiments, the registration process is performed between the video frame generated by the first image capturing device 2D and render point map image and by finding associated points in the 3D point cloud.

In some embodiments, the first and second image capturing devices are co-located at a rigid frame.

In some embodiments, the first image capturing device includes a monocular camera and the second image capturing device includes a 3D camera.

In some embodiments, the rigid frame fixes a relative position of the first and second image capturing devices.

In some embodiments, the remote measurement processing system determines the depth between the two points selected from the 2D image by determining a difference between z coordinates of x,y,z coordinates of the associated points in the 3D point cloud.

In some embodiments, the remote measurement processing system determines the length between the two points selected from the 2D image by determining all points in the 3D point cloud which are located along the line connecting the two points selected from the 2D image, then calculating the length between each pair of the points in the 3D point cloud using the x,y,z coordinates in the 3D point cloud, and adding the calculated lengths.

In another aspect, a method for measuring the difference between z-values of two points of an image of a region of interest of a telemedicine patient comprises selecting two points on a displayed 2D video frame; inputting point data of the two points to a remote measurement processing unit; transforming coordinates of the selected two points of the point data to coordinates of a local 2D high resolution camera; transforming the coordinates of the local 2D high resolution camera to coordinates in a 3D point cloud; and calculating the depth of the region of interest in the 3D point cloud by calculating the difference between z coordinates.

In some embodiments, a z difference between the two points is a depth.

In some embodiments, the distance between two points in 3D point cloud is a length, and wherein the method comprises measuring the length of the two point by calculating all identified points in the 3D point cloud which are located along a line connecting two points in 2D video, calculating the length between every pair using their x,y,z coordinates in 3D point cloud, and adding the calculated lengths together to finalize the measurement of the length in 3D.

In some embodiments, the method further comprises calibrating the local 2D high resolution camera and a 3D camera generating the point cloud.

BRIEF DESCRIPTION OF THE SEVERAL VIEWS OF THE DRAWINGS

The above and further advantages may be better understood by referring to the following description in conjunction with the accompanying drawings, in which like numerals indicate elements and features in various figures. The drawings are not necessarily to scale, emphasis instead being placed upon illustrating the principles of the concepts.

DETAILED DESCRIPTION

Figure 1:
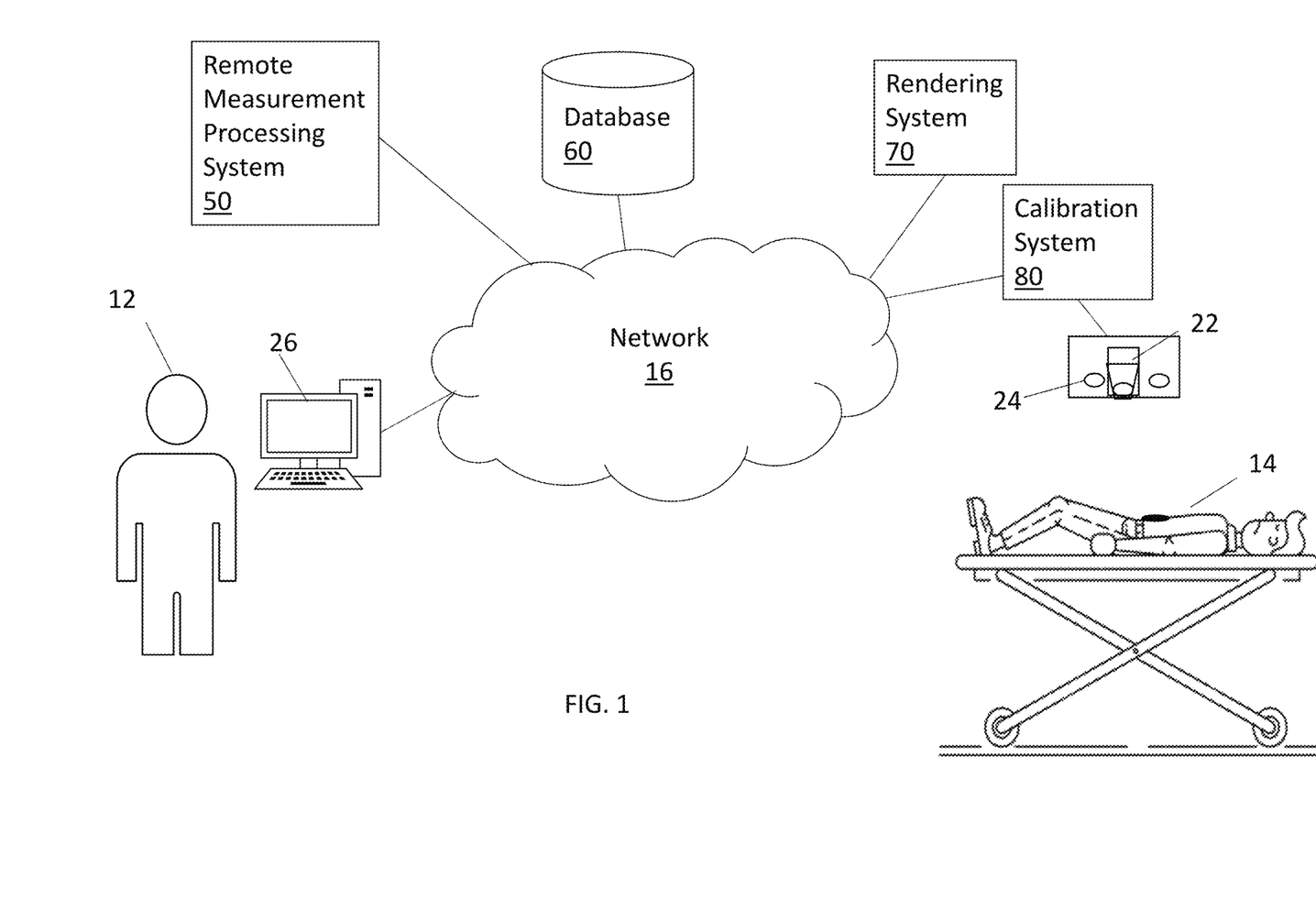
FIG. 1 is a diagram illustrating a telemedicine environment in which aspects of the present inventive concepts may be practiced.

FIG. 1 is a diagram illustrating a telemedicine environment in which aspects of the present inventive concepts may be practiced. An overall system including a rendering system 70, a calibration system 80, and a remote measurement processing system 50 may be implemented in the telemedicine environment. The telemedicine environment may include one location that includes a medical professional, teacher, doctor, nurse, and so on, and another location that includes a patient, student, or other user, or other applications that include the electronic exchange of information between remote computer users.

Two image capturing devices, in particular, a monocular camera 22 and a three-dimensional (3D) camera 24, are co-located with a patient 14 at a location remote from a doctor 12 or other medical professional. The monocular camera 22 and 3D camera 24 are preferably co-located under a common frame, housing, enclosure, or the like, for example, a rigid frame, so that the relative positions of the cameras 22, 24 are fixed and remain constant during movement, for example, where the cameras 22, 24 capture various images of an object scene. The calibration of the cameras 22, 24 permits the system to find parameters and establish a unified coordinate system.

The monocular camera 22 and 3D camera 24 operate collectively to capture 2D and 3D images, or video, during a measurement scan of an object scene, for example, a region of interest of a patient, more specifically, images of a wound, incision, skin lesion, or the like. More specifically, the monocular camera 22 produces real-time or near real-time 2D images, e.g., high 2D resolution video, during a medical procedure, which may be transmitted via a network 16 to a computer 26 having a display at a remote location, where a medical practitioner such as a doctor, nurse, or the like can observe the displayed 2D video, and may annotate or otherwise modify the displayed video using augmented reality tools or the like that are executed by a computer peripheral device such as a mouse/cursor, touchscreen, voice-activated commands and so on. Therefore, in particular, the user can select points on the displayed 2D video during a remote medical procedure, for example, to identify points on the video, or one or more images or frames of the video, for determining a depth, length, or related measurement.

The 3D camera 24 collocated with the 2D camera 22 collects 3D data from the same object scene as the 2D camera. A point cloud may be produced from the 3D video images captured of the object scene, which when combined with 2D video data, i.e., pertaining to a field of view (FOV) common to both cameras 22, 24, may be used for generating depth or length measurements during a remote medical procedure. To achieve this, the cameras 22, 24 are calibrated for finding relevant parameters and establishing a unified coordinate system, described below.

In some embodiments, the telemedicine environment shown in FIG. 1 includes a remote measurement processing unit 50 that communicates with the cameras 22, 24, and/or other electronic devices such as a database 60, rendering system 70, calibration system 80, and/or user computers 26 via a communications network 16. In some embodiments, the rendering system 70 is part of, i.e., stored and executed, at one of the cameras 22, 24 or the remote measurement processing unit 50. The network 16 may be a public switched telephone network (PSTN), a mobile communications network, a data network, such as a local area network (LAN) or wide area network (WAN), e.g., 3G/4G/5G network, or a combination thereof, or other data communication network known to those of ordinary skill in the art.

The remote measurement processing unit 50 performs a measurement of a length and/or depth of an object, such as a wound of a patient for the remote doctor or other viewer and present it in a computer display 26.

Figure 2:
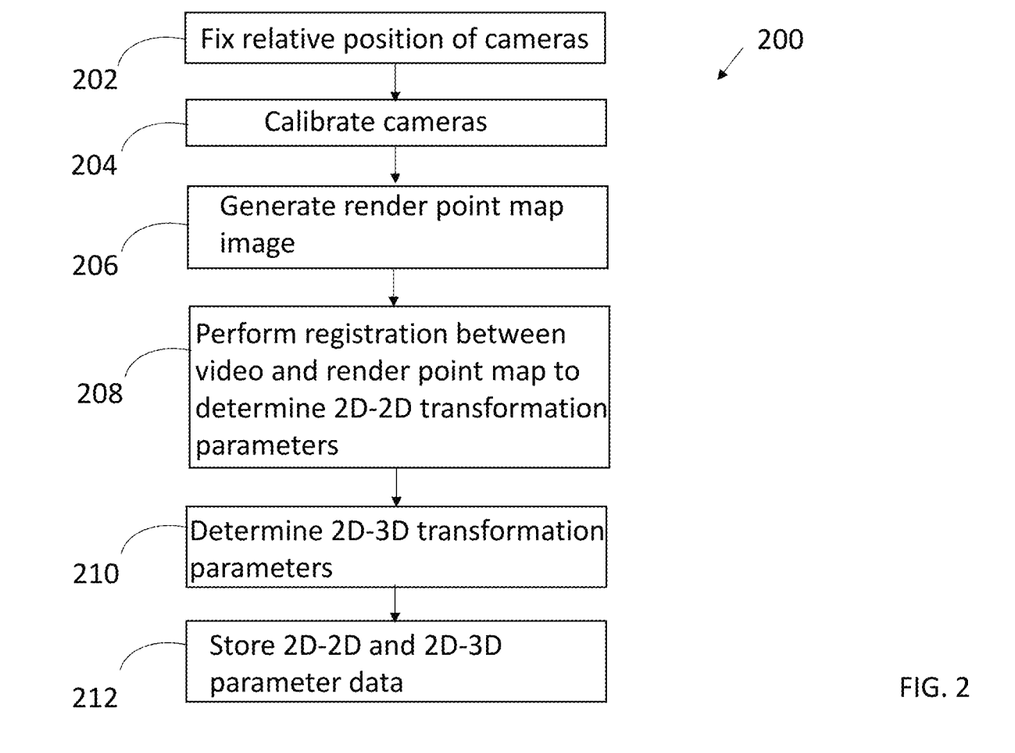
FIG. 2 is a flow diagram of a method for initializing a remote measurement processing system to determine a measurement taken from a digital image in a telemedicine operation, in accordance with some embodiments.

FIG. 2 is a flow diagram of a method 200 for initializing the remote measurement processing system 50 of FIG. 1 to determine a measurement taken from a digital image in a telemedicine operation, in accordance with some embodiments.

More specifically, method 200 locates the selected points of live video in a 3D point cloud and determines a distance between the selected points or determines a depth. In describing the method 200, reference is made to FIG. 1. For example, some or all of the method 200 may be performed by the remote measurement processing unit 50, image capturing devices 22, 24, rendering system 70, calibration system 80, and/or other elements of the telemedicine environment shown and described with reference to FIG. 1.

At block 202, the two image capturing devices, namely, the monocular camera 22 and 3D camera 24, are coupled to and collocated at a rigid frame or other apparatus that fixes and maintains a relative position of the monocular camera 22 and 3D camera 24.

At block 204, the monocular camera 22 and 3D camera 24, once in a fixed position, are calibrated to produce intrinsic and extrinsic parameters, which in turn are used to create an accurate render point map. To achieve the foregoing, a well-known camera calibration technique may be performed, for example, using a checkerboard target and non-linear optimization. Intrinsic parameters may include but not limited to camera parameters such as focal length, principal point, skew coefficients, optical center or principal point, or other camera characteristics or features. Extrinsic parameters correspond to rotation and translation vectors used to transform 3D point coordinates to a point in another coordinate system, for example transforming a point from world coordinate system to camera coordinate system. The intrinsic and extrinsic parameters of the cameras 22, 24 along with calibration data can be stored at the database 60.

The calibration method starts by using the cameras 22, 24 to capture a set of calibration images of the checkerboard target or other calibration object with a known pattern. The images are captured at various positions, orientations, angles, and so on. This provides an extensive set of views of the calibration object from a variety of viewpoints. The intrinsic and extrinsic camera parameters can then be determined. The calibration method utilizes sets of sequences of images of the calibration object.

At block 206, a set of fiducial markers are used as reference points in a generated render point map image, or an overlay of video images observable by both the monocular camera 22 and 3D camera 24, i.e., in an image viewer having a common FOV to determine relevant x-y coordinates. The fiducial markers can be any 3D objects placed in the field of view of each of the monocular camera 22 and 3D camera 24, and which appear in the image produced, for use as a reference. Fiducial markers positioned on a calibration board or the like may permit semi-automatic or fully automatic registration. In other words, the render point map image maps a 3D point cloud of a marker produced by the 3D camera 24 to a shared field of view (FOV) of the cameras 22, 24 to register the video with the image of render point map and determine the set of 2D to 2D transformation parameters.

At block 208, the 2D video taken by the monocular camera 22 of the markers is used by the rendering system 70 to transform the point coordinates selected from the video to render point map image and find them in 3D point cloud using a search algorithm and 2D-3D transformation parameters described in block 210. For example, a registration procedure may be performed between two captured images. By finding associated points in an image of a render point map and video frame generated by the 2D camera 22, two images can be registered, i.e., the render point map is registered with a 2D image or video frame, and transformation parameters using the corresponding point coordinates may be determined. Registration in this manner provides such an improvement to the effectiveness and quality of the images. The highly precise calibration creates submillimeter to a millimeter accuracy, or more precise accuracy, in measurements. The calibration parameters are used to create render point map image with high precision. The registration creates parameters to transform coordinates of the points from 2D camera to 3D point cloud. Hence, this method of calibration, point map creation, and registration creates a unified system for 2D and 3D camera to generate high precision measurement from different views, orientations, distances, and angles for telemedicine applications.

At block 210, a set 2D to 3D transformation parameters are determined as part of the abovementioned registration procedure. The transformation step here includes connecting captured 2D images of the fiducial markers to a pre-acquired 3D reference volume, or point cloud to produce the transformation parameters. More specifically, the 3D point cloud of the fiducial markers (as viewed by the camera FOV) is used to determine relationship data between the render point map and the point cloud, which may include transformation parameters. Thus, the relationship between the render point map and 3D point cloud is also identified using the position of the fiducial markers.

At block 212, the registration data such as 2D-2D transformation parameters, 2D-3D transformation parameters, and calibration data captured in the previous steps are stored at the database 60 or other storage repository.

Figure 3:
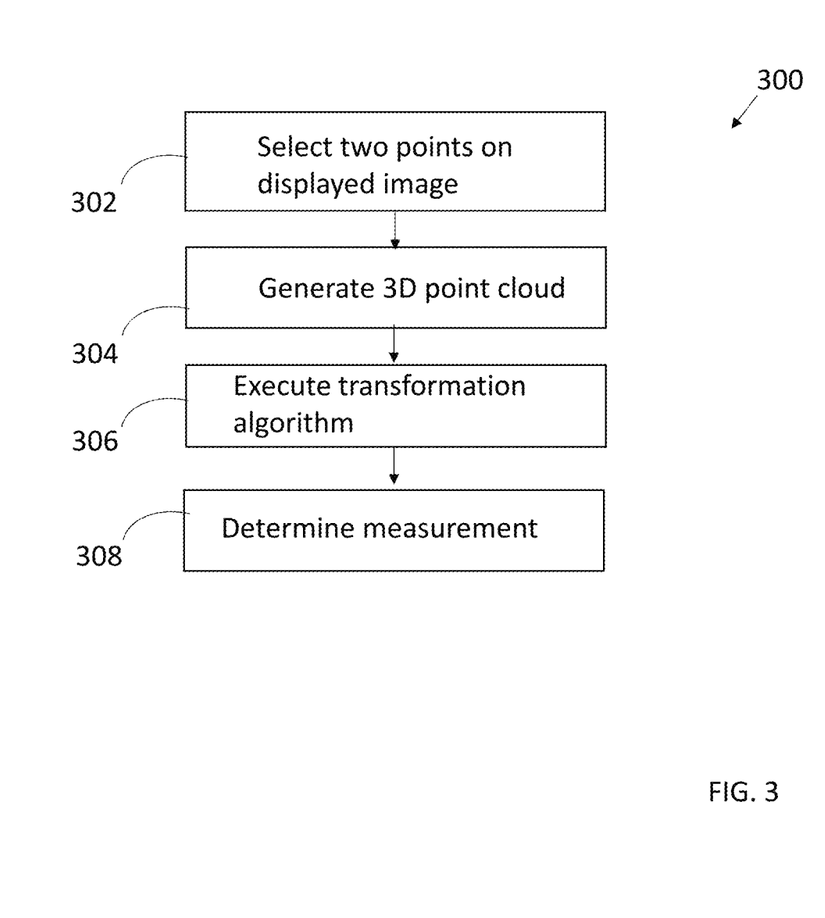
FIG. 3 is a flow diagram of a method for remotely measuring a displayed medical scene of interest, in accordance with some embodiments.

FIG. 3 is a flow diagram of a method 300 for remotely measuring a depth or length of a wound in a patient, in accordance with some embodiments. In performing the method 300, data generated by method 200 in FIG. 2 may be used. Thus, method 300 is performed after method 200. Some or all of the method 300 may be performed by the remote measurement processing unit 50, image capturing devices 22, 24, rendering system 70, and/or other elements of the telemedicine environment shown and described with reference to FIG. 1.

Figures 4, 5:
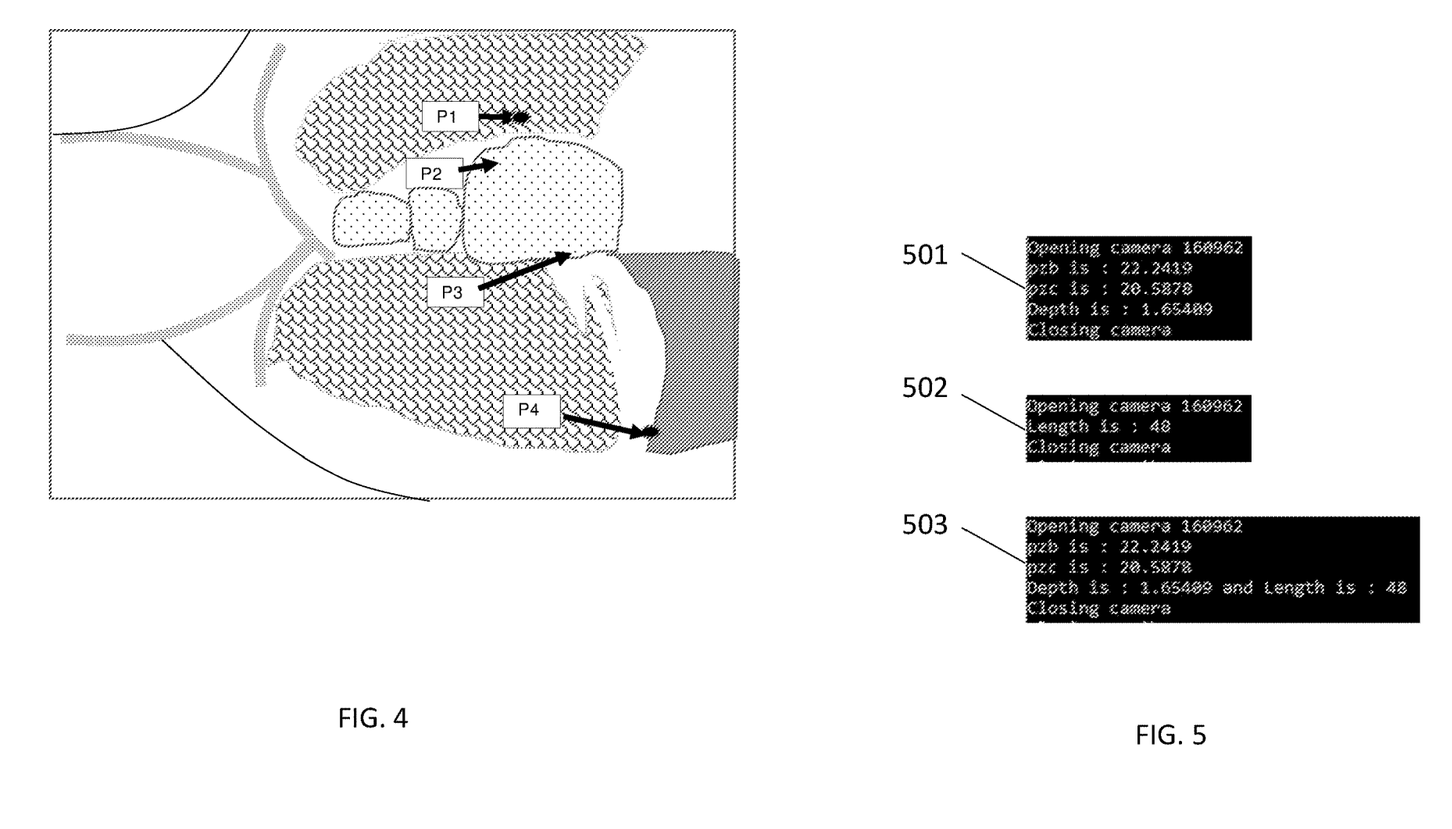
FIG. 4 is a view of a displayed video image from which two points are selected for determining a measurement, in accordance with some embodiments.
FIG. 5 is a view of a displayed measurement result produced in accordance with some embodiments.

At block 302, a user 12, for example, a remote medical professional such as a surgeon, selects two points on an image of a live 2D video feed displaying patient (e.g. patient's wound) at the user's computer 26, for example, shown in FIG. 4. As described above, the monocular camera 22 generates live video, i.e., real-time or near real-time caused by network delays or the like, during a surgery and the user 12 can at the computer 26 observe the video, click on it, and/or use augmented reality or other overlay tools to annotate or otherwise draw on the video. The user 12 may click the first point on the wound or any other area of interest for depth measurement, then click on a region of the displayed image of the patient 14, or a point near the wound or other area of interest of the displayed patient 14 to provide the second point. The difference between z coordinates of the two selected points in the 3D point cloud is the depth of the wound or depth of the area of interest, where the z coordinates are part of a Cartesian coordinate system or other 3D reference. The length may also, or instead be calculated by identifying points in the 3D point cloud which are located along the line connecting the two points in 2D video.

At block 304, a point cloud is produced by the 3D camera 24 of the wound or other area of interest, which captures 3D images in the same FOV as the 2D camera 22.

At block 306, a transformation algorithm is executed. More specifically, computer code including software or program instructions executed by the remote measurement processing system 50 may implement the transformation algorithm. In doing so, the remote measurement processing system 50 searches the point cloud to find the points in the point cloud generated by the 3D camera during the surgery, and identifies the associated 2D points along a curve in the 3D point cloud.

More specifically, the coordinates of the two selected points are transformed to associated coordinates of the render point map regarding the monocular camera 22 processed in method 200 or 300. Here, adjusted x and y coordinates of the selected points are identified. A transformation algorithm is applied to find the associated points in the render point map generated in the method 200. The algorithm searches the generated point cloud to find the corresponding points in the point cloud generated by the 3D camera during the surgery, for example, in the same FOV as the 2D camera 22 producing the video shown in FIG. 5. The coordinates of the points of the 2D camera 22 in turn are transformed to x and y coordinates of corresponding points in the 3D point cloud using the established registration data, for example, transformation parameters such as rotation, translation, and scaling parameters determined and stored in method 200. In addition, a z coordinate is identified for each relevant x-y coordinate.

At block 308, a measurement is determined. The system may provide a selection option, for example, provided to a user computer for a user to select between a depth measurement (e.g., points P1 and P2 shown in FIG. 4) and a length measurement (e.g., points P3 and P4 shown in FIG. 4). The difference between the z coordinates of the two points in the point cloud represents the depth of the selected point, for example, selected points P1 and P2 shown in FIG. 4. For example, A depth result 501 and length result 502 are presented in a display, for example, shown in FIG. 5. Also displayed are z coordinates (pzb, pzc) of the two points.

The length between two points, for example, the distance between points P3 and P4 shown in FIG. 4 and displayed in FIG. 5, is determined by identifying the associated 2D points along a curve in the generated 3D point cloud in order to find the distance between the points in the 3D point cloud where the distance is a curve in a 3D environment. To measure a length between two points, the user 12 may select the two points by clicking on two points of interest in display of computer 26. The length is calculated by finding all points in 3D point cloud which are located along the line connecting two points in 2D video. Then the length between every pair (e.g. point j and point j+1) is calculated using their x,y,z coordinates in the 3D point cloud. All the lengths are added together to finalize the measurement of the length in 3D.

While concepts have been shown and described with reference to specific preferred embodiments, it should be understood by those skilled in the art that various changes in form and detail may be made therein without departing from the spirit and scope as defined by the following claims.

What is claimed is:

1. A system for performing a telemedicine operation, comprising:
a rendering system that processes image data collected at a common field of view (FOV) at a first location by a monocular camera and a 3D camera, the image data including a combination of two-dimensional (2D) and three-dimensional (3D) images of a region of interest at the common FOV at the first location;
a first computer that produces a 3D point cloud from the 3D images, the 3D point cloud providing reference values for adjusting coordinates of two points selected of a 2D image of the 2D images that is displayed at a second location remote from the first location; and
a second computer that processes the adjusted coordinates of the selected two points to determine a difference between the two points, and calculates at least one of a length or depth of the region of interest from the difference between the two points.

2. The system of claim 1, further comprising an overlay system that creates a render point map image from the image data, wherein the render point map image maps the 3D point cloud to the common FOV of the monocular camera and the 3D camera.

3. The system of claim 2, wherein the second computer transforms the coordinates of the selected two points to associated coordinates of the render point map image to identify the adjusted coordinates of the selected two points.

4. The system of claim 2, wherein the coordinates of the render point map image are generated prior to the selection of the two points, and processed to identify z coordinates of the selected to points from the 3D point cloud.

5. The system of claim 2, wherein the render point map image is registered with a 2D image at a display window that displays the 2D image captured by the monocular camera in the common FOV.

6. The system of claim 5, wherein the rendering system registers a 2D scene in the common FOV with the render point map image by capturing images including a set of fiducial markers in the common FOV to determine a set of registration parameters, which in turn are used to identify associated coordinates of the coordinates of the selected two points in the render point map image.

7. The system of claim 1, wherein the fiducial markers are 3D fiducial markers, and wherein images of the 3D fiducial markers mapped to the 3D point cloud.

8. A system that performs a telemedicine operation according to the steps of:
processing image data collected at a common field of view (FOV) at a first location, the image data including a combination of two-dimensional (2D) and three-dimensional (3D) images of a region of interest at the common FOV at the first location;
producing a 3D point cloud from the 3D images, including providing reference values for adjusting coordinates of two points selected of a 2D image or video frame of the 2D images that is displayed at a second location remote from the first location; and
processing the adjusted coordinates of the selected two points to determine a difference between the two points; and
calculating a depth of the region of interest from the difference between the two points.

9. The system of claim 8, wherein adjusting the coordinates include transforming the coordinates of the selected two points to coordinates of a local 2D high resolution camera producing the 2D images, wherein the coordinates of the selected two points are identified for adjustment in response to transforming the coordinates of the two selected points to associated coordinates of a pre-generated 2D render point map image; and
using the transformed coordinates of the pre-generated 2D render point map image to search the 3D point cloud and identify associated z coordinates of each point.

10. The system of claim 8, wherein determining the difference between the two points includes calculating the depth of the region of interest in the 3D point cloud by calculating the difference between z coordinates.

11. The system of claim 8, further comprising creating a render point map image from the image data, wherein the render point map image maps the 3D point cloud to the common FOV.

12. The system of claim 8, wherein the coordinates of the render point map image are generated prior to the selection of the two points, and processed to identify z coordinates of the selected to points from the 3D point cloud.

13. The system of claim 9, wherein processing the adjusted coordinates of the selected two points includes determining a depth or length between the two points.

14. A system for performing a telemedicine operation, comprising:
a rendering system that processes image data collected at a common field of view (FOV) at a first location by a monocular camera and a 3D camera, the image data including a combination of two-dimensional (2D) and three-dimensional (3D) images of a region of interest at the common FOV at the first location;
a first computer that produces a 3D point cloud from the 3D images, the 3D point cloud providing reference values for adjusting coordinates of two points selected of a 2D image of the 2D images that is displayed at a second location remote from the first location; and at least one fiducial marker in the common FOV used as reference points in the 2D render point map image;

a second computer that maps the 3D point cloud of a fiducial marker of the at least one fiducial marker to the common FOV to register a 2D video of the fiducial marker with a render point map image generated by the first computer processes the adjusted coordinates of the selected two points to determine a difference between the two points; and an overlay system that generates and stores a 2D render point map image from a unified view of the common FOV.

15. The system of claim 14, wherein the unified view includes an overlay of overlays a 2D image with respect to at least one 2D video frame.

16. The system of claim 14, wherein the render point map image maps a 3D point cloud of a marker produced by the 3D camera to a shared field of view (FOV) to register the video with the image of render point map and determine the set of 2D to 2D transformation parameters.

17. The system of claim 14, wherein the second computer determines the difference including a depth or length between the two points.

* * * * *